United States Patent [19]

Philippe et al.

[11] Patent Number: 5,004,733

[45] Date of Patent: Apr. 2, 1991

[54] ESTERS OF THE ETRETINIC TYPE OR RELATED TO MACROLIDIC AND LINCOSAMIDIC ANTIBIOTICS AND PHARMACEUTICAL AND COSMETIC COMPOSITIONS CONTAINING SAID ESTERS

[75] Inventors: Michel Philippe, Antony; Henri Sebag, Paris, both of France

[73] Assignee: Societe Anonyme Dite: L'Oreal, Paris, France

[21] Appl. No.: 266,611

[22] Filed: Nov. 3, 1988

[30] Foreign Application Priority Data

Nov. 4, 1987 [LU] Luxembourg .............................. 87035

[51] Int. Cl.⁵ ...................... A61K 31/70; C07H 15/16; C07H 17/08

[52] U.S. Cl. ..................................... 514/029; 536/7.1; 536/7.2; 536/16.2; 514/859; 514/863; 514/24; 514/30; 514/844

[58] Field of Search ........................ 536/7.1, 7.2, 16.2; 514/24, 29, 30, 844, 859, 863

[56] References Cited

U.S. PATENT DOCUMENTS 4,575,497  3/1986  Omura et al. ......................... 514/30

OTHER PUBLICATIONS

European Search Report, Jun. 3, 1988.

*Primary Examiner*—Johnnie R. Brown
*Assistant Examiner*—Elli Peselev
*Attorney, Agent, or Firm*—Cushman, Darby & Cushman

[57] ABSTRACT

Esters of the etretinic type or related to macrolides and lincosamides are employed in the treatment of acne and psoriasis.

9 Claims, No Drawings

ESTERS OF THE ETRETINIC TYPE OR RELATED TO MACROLIDIC AND LINCOSAMIDIC ANTIBIOTICS AND PHARMACEUTICAL AND COSMETIC COMPOSITIONS CONTAINING SAID ESTERS

The present invention relates to esters of the etretinic type or related to antibiotics, principally macrolides and lincosamides, to a process for their preparation and to pharmaceutical or cosmetic compositions containing them for the treatment of various dermatoses, and principally in the treatment of acne and psoriasis.

More particularly, the esters in accordance with the present invention, are intended for the treatment of dermatoses, infectious or not.

In the treatment of acne, erythromycin among the macrolides as well as clindamycin among the lincosamides have been more particularly recommended, but their use requires (particularly for erythromycin) relatively high concentrations so as to obtain a satisfactory result.

Moreover, treatment with these antibiotics has proved, in certain cases, less effective, in the measure where certain strains of *propionibacterium acnes* have exhibited a progressive resistance in their regard.

The topical application of clindamycin and more particularly erythromycin collides, besides, with a problem of penetration through the corneum stratum limiting from this fact their efficacy.

The esters of antibiotics in accordance with the invention provide a satisfactory solution to the problem raised by the use of these antibiotics in the treatment of acne, in the measure where it is established that these esters have an activity on *propionibacterium acnes*, the main germ responsible for the inflammation phenomena of the skin.

The esters in accordance with the invention have from the fact of their structure a pronounced lipophilic character which facilitates a better penetration across the epidermis.

The new esters in accordance with the invention are well tolerated by the skin and are revealed to be much less toxic when taken orally than the antibiotic/acid combination.

Besides, they exhibit, with respect to known esters, the advantage of possessing a potential comedolytic activity due to the corresponding acid chain, which confers to these esters an image of a "prodrug".

The state of the art relative to esters of macrolides is represented principally by French patent No. 85.07287 (2.582.000) which relates to poly unsaturated fatty esters of erythromycin A such as the linoleate, and the linolenate of erythromycin A.

The state of the art relative to esters of lincosamides is represented principally by German patent No. 2.017.003 which describes the preparation of esters of lincomycin and clindamycin whose acyl chain has between 1 and 18 carbon atoms.

The present invention has for an object as a new industrial product, esters of the etretinic type or related to macrolides or lincosamides, said esters having the following general formula:

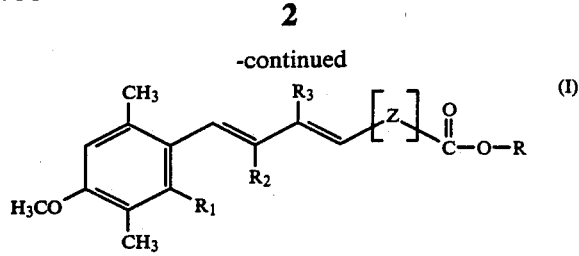

wherein

R represents a macrolide or a lincosamide radical, $R_1$ represents methyl, $R_2$ represents hydrogen, or $R_1$ and $R_2$ together form a vinylene radical (—CH=CH—), $R_3$ represents hydrogen or alkyl having 1–4 carbon atoms, and Z represents a divalent radical of the formula

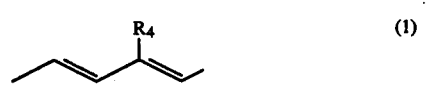

wherein $R_4$ represents hydrogen or alkyl having 1–4 carbon atoms, or

and the isomers, mixtures and salts of the said esters.

Representative macrolides include erythromycin A, roxithromycin, oleandomycin, josamycin and spiramycines I, II and III.

Representative lincosamides include lincomycin and clindamycin.

A—The esters of erythromycin A an roxithromycin can be represented by the formula

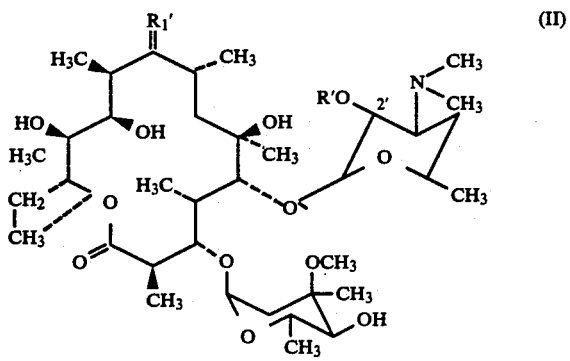

wherein $R'_1$ represents O (erythromycin A) or N~O—CH$_2$—O—CH$_2$—CH$_2$—O—CH$_3$ roxithromycin, and R' represents the following acyl radical:

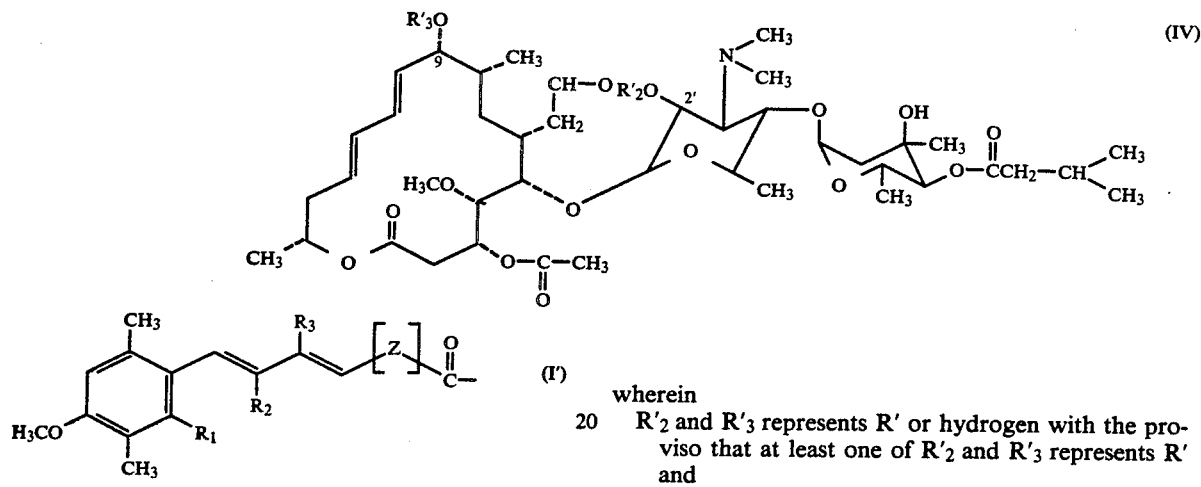

(I')

wherein
R₁, R₂, R₃ and Z have the same meanings given above.

These esters of erythromycin A and roxithromycin are those in position 2'.

B—The esters of oleandomycin can be represented by the following formula:

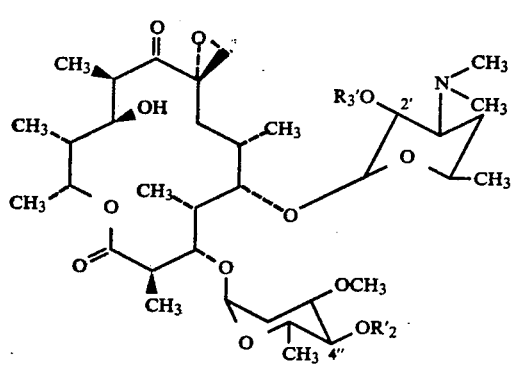

(III)

wherein
$R'_2$ and $R'_3$ represents R' or hydrogen with the proviso that at least one of $R'_2$ and $R'_3$ represents R', and
R' has the same meaning given above.

These esters are those in position 2' and/or 4", but they can be provided in the form of a mixture.

C—The esters of josamycin can be represented by the following formula:

(IV)

wherein
$R'_2$ and $R'_3$ represents R' or hydrogen with the proviso that at least one of $R'_2$ and $R'_3$ represents R' and
R' has the same meaning given above.

These esters are those in position 9 and/or 2', but they can be provided in the form of a mixture.

D—The esters of spiramycins can be represented by the following formula:

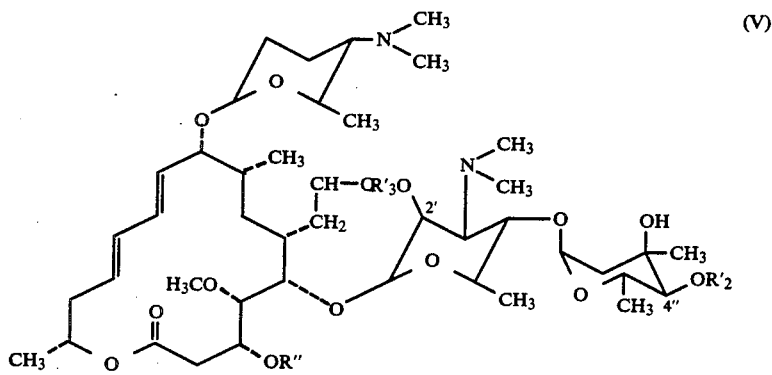

(V)

wherein
$R'_1$ or $R'_3$ represent R' or hydrogen with the proviso that at least one of $R'_2$ and $R'_3$ represents R' and
R' has the same meaning given above and
R" represents hydrogen (spiramycin I), acetyl (spiramycin II) or propionyl (spiramycin III).

These esters of spiramycin (I), (II) and (III) are those in position 2' and/or 4" and they can be provided in the form of a mixture.

E—The esters of lincomycin and clindamycin can be represented, respectively, by the following formulas (VI) and (VII):

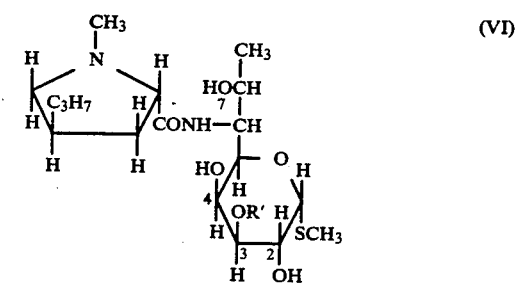

(VI)

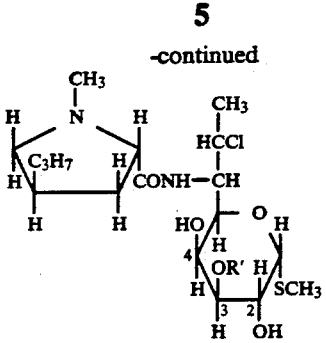

(VII)

wherein

R' has the same meaning given above.

The esters of lincomycin (VI) and clindamycin (VII) are preferably those in position 3. However, they can be provided in the form of mixtures with the esters in position 2, 4 and 7 of lincomycin and with esters in position 2 and 4 of clindamycin. Representative esters of formula I, in accordance with the invention, include the following:

O-etretinoyl (all trans)-2'-roxithromycin,
O-etretinoyl (all trans)-2'-erythromycin A,
O-etretinoyl (all trans)-3-lincomycin,
O-etretinoyl (all trans)-3-clindamycin,
O-etretinoyl (all trans)-2'-oleandomycin,
O-etretinoyl (all trans)-2'and 9-josamycin,
O-etretinoyl (all trans)-2'-spiramycin (I), (II) and (III),
O-2'-[7-(5,8-dimethyl-6-methoxy-2-naphthyl)-3-methyl-2E, 4E, 6E octatrienoyl]-erythromycin A,
O-2'-[7-(5,8-dimethyl-6-methoxy-2-naphthyl)-3-methyl-2E, 4E, 6E octatrienoyl]-oleandomycin,
O-2'-[[4-(2,3,6-trimethyl-4-methoxy phenyl)-2-methyl-1E, 3E butadiene]-yl-4-benzoyl]-erythromycin A,
O-3[[4-(2,3,6-trimethyl-4-methoxy phenyl)-2-methyl-1E, 3E butadiene]-yl-4-benzoyl]-clindamycin,
O-2'[7-(5,8-dimethyl-6-methoxy-2-naphthyl)-3-methyl-2E, 4E, 6E octatrienoyl]-roxithromycin, and
O-2'[[4-(2,3,6-trimethyl-4-methoxy phenyl)-2-methyl-1E, 3E butadiene]-yl-4-benzoyl]-roxithromycin.

The present invention also relates to a process for preparing the esters of formula (I) according to the present invention.

Various procedures for esterification can be employed, but preferably this esterification is carried out in an anhydrous organic solvent medium, preferably in tetrahydrofuran alone or in mixture with another organic solvent such as pyridine, by reacting an excess of mixed anhydride of the formula:

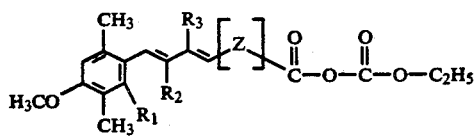

wherein $R_1$, $R_2$, $R_3$ and Z have the same meanings given above, the said anhydride being prepared in situ, (for example starting with ethyl chloroformate and the corresponding acid) with a macrolide or lincosamide in base form, in the presence of an organic or mineral base such as pyridine and/or sodium bicarbonate and/or triethylamine.

This method with mixed anhydride permits to obtain preferentially esters in position 2' of macrolides and/or in position 9 principally for josamycin and/or in position 4" principally for the spiramycins and the esters in position 3 of lincosamides in good yield conditions.

The other procedures of esterification principally of lincomycin and clindamycin by the method using imidazolides of corresponding acids in an anhydrous solvent such as N,N-dimethylformamide in the presence of a base such as sodium or potassium tert. butylate lead to a mixture of esters of these antibiotics.

The present invention also relates to pharmaceutical composition that can be administered topically, orally, parenterally or rectally as well as to cosmetic compositions for the treatment of various dermatoses, principally acne and psoriasis, these compositions being provided in anhydrous form and containing at least one ester in accordance with the invention, such as defined above, in an amount ranging from 0.001 to 10 weight percent, but preferably from 0.01 to 1 weight percent, based on the total weight of the composition.

For the preparation of compositions, according to the invention, containing as the active component, at least one ester according to the invention such as defined above, there can be employed vehicles and adjuvants described in the literature of pharmaceuticals, cosmetics and related fields.

For the preparation of solutions, there can be employed, for example, an acceptable organic solvent from a physiologic view point.

The acceptable organic solvent is selected principally from the group consisting of acetone, isopropyl alcohol, triglycerides of fatty acids, $C_1$-$C_4$ alkyl esters of short chain acids, polytetrahydrofuran ethers and silicones such as cyclomethicones.

The compositions according to the invention can also include a thickening agent such as a cellulose derivative in an amount ranging from 0.5 to 20 weight percent based on the total weight of the composition.

The compositions according to the invention can also contain in combination with at least one ester according to the invention, at one other known anti-acne or anti-psoriasic agent.

If necessary, a conventional adjuvant selected from the group consisting of antioxidants, preservatives, perfumes and dyes can be added.

Representative useful antioxidants include, for instance, t-butylhydroxyquinone, butylhydroxy anisole, butylhydroxy toluene and α-tocopherol and its derivatives.

The pharmacologic and galenic transformations of the compounds of the present invention are effected in a known manner.

The galenic forms can be, for topical applications, creams, milks, gels, more or less thick lotions, lotion-impregnated pads, pomades, sticks or even aerosol formulations provided in the form of sprays or foams.

The compositions for oral administration ca be provided in the form of tablets, gelules, lozenges, syrups, suspensions, emulsions, powders, granules or solutions.

The compositions can also be provided in the form of suppositories.

The treatment of acne using the topical compositions of the invention comprises applying, two or three times each day, a sufficient amount on the areas of the skin being treated and this for a period of time ranging from 6 to 30 weeks and preferably from 12 to 24 weeks.

The compositions according to the invention can also be used as a preventative, i.e. on the areas of the skin susceptible of being attacked by acne or psoriasis.

There are now given, as an illustration, several examples of the preparation of esters of the etretinic type or related to antibiotics of formula (I) in accordance with the invention as well as several examples of pharmaceutical or cosmetic compositions for the treatment of dermatoses, principally of acne and psoriasis.

EXAMPLE 1

Preparation of 2'-O-etretinoyl (all trans) erythromycin A

In a round bottom flask, under an inert atmosphere, there are dissolved 5.9 g (16.6 mmoles) of etretinic acid (all trans) in 35 ml of anhydrous tetrahydrofuran; the reaction mixture is cooled to 0° C., and there are then added 2.3 ml (16.6 mmoles) of triethylamine and 1.6 ml (16.6 mmoles) of ethyl chloroformate. The solution is stirred for 5 minutes and there are added 15 ml of anhydrous pyridine, then 4.9 g (6.7 mmoles) of erythromycin A previously dissolved in 150 ml of tetrahydrofuran. The reaction mixture is continued to be stirred for 10 hours, and the temperature is permitted to return to ambient temperature (chromatography on thin layer silica gel: methylene chloride (90)/methanol (10)). The solution is poured into 60 ml of water, then extracted with ethyl acetate. The organic phase is dried on magnesium sulfate, filtered, and then concentrated under a partial vacuum. The crude product thus obtained is chromatographed on silica gel (HPLC) by using as the eluant: ethyl acetate (7)/hexane (3) to result in the isolation of 4.6 g (65% yield) of pure 2'-O-etretinoyl (all trans)-erythromycin A.

M.P.=137° C. (hexane/ethyl acetate)
$[\alpha \pi_D{}^{22}] = -80°$ C. (C=3mg/ml-dichloromethane)

| Microanalysis: $C_{60}H_{95}NO_{15}.2.5H_2O$; M.W. = 1115.5 | | | |
|---|---|---|---|
| | C | H | N |
| Calculated, % | 64.6 | 9.03 | 1.26 |
| Found, % | 64.2 | 8.63 | 1.24 |

NMR $^{13}C$ (CDCl$_3$, internal ref. T.M.S.)
Negative $\gamma$ effects in 1'(−2 ppm) and 3'(−2.1 ppm) indicating the ester in the 2' position.

EXAMPLE 2

Preparation of 3-0-etretinoyl (all trans) lincomycin

In a round bottom flask, under an inert atmosphere, there are dissolved 5.9 g (16.6 mmoles) of etretinic acid (all trans) in 30ml of anhydrous tetrahydrofuran; the reaction mixture is cooled to 0° C., and there are then added 2.3 ml (16.6 mmoles) of triethylamine and 1.6 ml (16.6 mmoles) of ethyl chloroformate; the solution is stirred for 5 minutes and there are added 15 ml of anhydrous pyridine, then 2.2 g (5.4 mmoles) of lincomycin previously dissolved in 100 ml of a tetrahydrofuran (7)/pyridin (3) mixture. The reaction mixture is continued to be stirred for 10 hours, and the temperature is permitted to return to ambient temperature (chromatography on thin layer silica gel: methylene chloride (90)/methanol (10)). The solution is poured into 100 ml of water, then extracted with ethyl acetate. The organic phase is dried on magnesium sulfate, filtered, and then concentrated under a partial vacuum. The crude product thus obtained is chromatographed on a silica gel column (HPLC) by using as the eluant: ethyl acetate (8)/hexane (2) to result in the isolation of 2.4 g (60% yield) of 3-0-etretinoyl (all trans) lincomycin with a trace of another position isomer.

M.P.=98° C. (hexane/ethyl acetate)

| Microanalysis: $C_{41}H_{62}N_2O_8S.1.5H_2O$; MW = 770.03 | | | |
|---|---|---|---|
| | C | H | N |
| Calculated, % | 63.95 | 8.5 | 3.64 |
| Found, % | 63.54 | 7.9 | 3.68 |

NMR $^{13}C$ (CDCl$_3$, internal ref. T.M.S.) confirms the structure and the regioselective of the esterification.

EXAMPLE 3

Preparation of 3-O-etretinoyl (all trans) clindamycin

In a round bottom flask, under an inert atmosphere, there are dissolved 5.9 g (16.6 mmoles) of etretinic acid (all trans) in 30 ml of anhydrous tetrahydrofuran; the reaction mixture is cooled to 0° C., and there are then added 2.3 ml (16.6 mmoles) of triethylamine and 1.6 ml (16.6 mmoles) of ethyl chloroformate; the solution is stirred for 5 minutes, and there are added 15 ml of anhydrous pyridine, then 2.35 g (5.5 mmoles) of clindamycin previously dissolved in a tetrahydrofuran (8)/pyridine (2) mixture. The reaction mixture is continued to be stirred for 10 hours and the temperature is permitted to return to ambient temperature (chromatography on thin layer silica gel; methylene chloride (95)/methanol (5)). The solution is poured into 80 ml of water and then extracted with ethyl acetate. The organic phase is dried on magnesium sulfate, filtered, and then concentrated under partial vacuum. The crude product thus obtained is chromatographed on a silica gel column (HPLC) by using as the eluant: ethyl acetate (5)/hexane (5) to result in the isolation of 2.7 g (65% yield) of 3-O-etretinoyl (all trans)-clindamycin and a trace of an isomer.

M.P.=92° C. (hexane/ethyl acetate)

| Microanalysis: $C_{41}H_{61}ClO_7N_2S.1H_2O$; MW = 779.48 | | | |
|---|---|---|---|
| | C | H | N |
| Calculated, % | 63.18 | 8.14 | 3.59 |
| Found, % | 63.08 | 8.05 | 3.40 |

NMR$^{13}C$ (CDCl$_3$, internal ref. T.M.S.)
The position of the ester is indicated by the $\beta$ positive effect in 3 (+1.5 ppm) and the $\gamma$ negative effects in 2 (−2.2 ppm) and 4 (−3 ppm).

EXAMPLE 4

Preparation of 2'-O-[7-(5,8-dimethyl-6-methoxy-2-naphthyl)-3methyl-2E, 4E, 6E octatrienoyl-] -erythromycin A In a round bottom flask, under an inert atmosphere, there are dissolved 500 mg (1.48 mmole) of 7-(5,8-dimethyl-6-methoxy-2-naphthyl)-3-methyl-2E, 4E, 6E-octatrienoic acid in 15 ml of anhydrous tetrahydrofuran; the reaction mixture is cooled to 0° C., and there are added 0.2 ml of triethylamine and 0.16 g (1.48 mmole) of ethyl chloroformate; the solution is stirred for 1 hour and there are added 0.25 ml of anhydrous pyridine, then 452 mg (0.62 mmole) of erythromycin A previously dissolved in 20 ml of tetrahydrofuran. The reaction mixture is continued to be stirred for 10 hours and the temperature is permitted to return to ambient temperature (chromatography on thin layer silica gel: methylene chloride, 90%/methanol, 10%). The solution is poured into 30 ml of water, and then extracted with ethyl acetate. The organic phase is dried on magnesium sulfate, filtered and then concentrated under a partial vacuum. The crude product thus obtained is chromatographed on a silica gel column (HPLC) by using as the eluant: ethyl acetate (7)/hexane (3) to result in the isolation of 320 mg (50% yield) of 2'-O-[7-(5,8-dimethyl-6-methoxy-2-naphthyl-] -3-methyl-2E, 4E, 6E-octatrienoyl-erythromycin A and a trace of an isomer thereof.

M.P.=135° C. (ethyl acetate/heptane)

| Microanalysis: $C_{59}H_{89}NO_{15}$; M.W. = 1052.4 | | | |
|---|---|---|---|
| | C | H | N |
| Calculated, % | 67.33 | 8.52 | 1.33 |
| Found, % | 67.33 | 8.22 | 1.18 |

NMR $^{13}$C (CDCl$_3$, internal ref. T.M.S.)

Negative γ effects in 1'(−2.1 ppm) and 3' (−2.1 ppm) indicates the position of the ester at 2'.

EXAMPLE 5

Preparation of
2'-O-[7-(5,8-dimethyl-6-methoxy-2-naphthyl)-3-methyl-2E, 4E, 6E-octatrienoyl]-roxithyromycin In a round bottom flask, under an inert atmosphere, there are dissolved 700 mg (2.15 mmoles) of 7(5,8-dimethyl-6-methoxy-2-naphthyl)-3-methyl-2E, 4E, 6E, -octatrienoic acid in 20 ml of anhydrous tetrahydrofuran; the reaction mixture is cooled to 0° C., and there are added 0.3 ml of triethylamine and 0.24 g (2.15 mmoles) of ethyl chloroformate; the solution is stirred for 1 hour and there is added 0.35 ml of anhydrous pyridine, and then 720 mg (0.86 mmole) of roxithromycin previously dissolved in 25 ml of tetrahydrofuran. The reaction mixture is then stirred for 10 hours and the temperature is permitted to return to ambient temperature (chromatography on thin layer silica gel: methylene chloride 90%/methanol 10%). The solution is poured into 40 ml of water, and then extracted with ethyl acetate. The organic phase is dried on magnesium sulfate, filtered, and then concentrated under a partial vacuum. The crude product thus obtained is chromatographed on a silica gel column (HPLC) by using as the eluant: ethyl acetate (7)/hexane (3) to result in the isolation of 620 mg (62% yield) of 2'-O-[7-(5,8-dimethyl-6-methoxy-2-naphthyl)-3-methyl-2E, 4E, 6E octatrienoyl]roxithromycin and an isomer thereof.

$[\alpha]_D^{20} = -65°$ (C=2mg/ml, dichloromethane);
M.P.=111° C. (ethyl acetate/heptane)

| Microanalysis: $C_{63}H_{98}N_2O_{17}$; M.W. = 1155.5 | | | |
|---|---|---|---|
| | C | H | N |
| Calculated, % | 65.48 | 8.54 | 2.42 |
| Found, % | 65.48 | 8.51 | 2.41 |

NMR $^{13}$C (CDCl$_3$, internal ref. T.M.S.)

Negative γ effects in 1' (−2.3 pm) and 3'(−2 ppm) indicate the position of the ester at the 2' position.

EXAMPLE 6

Preparation of 2'-O-[[4-(2,3,6-trimethyl-4-methoxy phenyl)-2-methyl-1E, 3E-butadiene]yl-4-benzoyl]roxythromycin In a round bottom flask, under an inert atmosphere, there are dissolved 500 mg (1.49 mmole) of 4-[4-(2,3,6-trimethyl-4methoxy phenyl)-2-methyl-1E, 3E-butadiene]-yl benzoic acid in 15 ml of anhydrous tetrahydrofuran; the reaction mixture is cooled to 0° C., and there are added 0.2 ml of triethylamine and 0.14 ml (1.49 mmole) of ethyl chloroformate; the solution is stirred for 1 hour and there are added 0.12 ml of anhydrous pyridine, then 415 mg (0.5 mole) of roxythromycin previously dissolved in 20 ml of tetrahydrofuran. The reaction mixture is then stirred for 10 hours and the temperature is permitted to return to ambient temperature (chromatography on thin layer silica gel: methylene chloride 90%/methanol 10%). The solution is poured into 35 ml of water, and then extracted with ethyl acetate. The organic phrase is dried on magnesium sulfate, filtered, and then concentrated under a partial vacuum. The crude product thus obtained is chromatographed on a silica gel column (HPLC) by using as the eluant: ethyl acetate (7)/hexane (3) to result in the isolation of 310 mg (55% yield) of 2'-O-[4-[4-(2,3,6trimethyl-4-methoxy phenyl)- 2-methyl-1E, 3E-butadiene]-yl benzoyl]-roxithromycin and a trace of an isomer thereof.

M.P.=108° C. (ethyl acetate/heptane)

| Microanalysis: $C_{63}H_{98}N_2O_{17}$; M.W. = 1155.52 | | | |
|---|---|---|---|
| | C | H | N |
| Calculated, % | 65.48 | 8.55 | 2.42 |
| Found, % | 64.96 | 8.31 | 2.35 |

NMR$^{13}$C (CDCl$_3$, internal ref. T.M.S.)

Negative γ effects in 1'(−2.5 ppm) and 3'(−1.7 ppm) indicate the position of the ester at the 2' position.

In accordance with the same operating procedures as described in Example 1 to 6, the other compounds listed above have also been prepared.

Pharmaceutical and Composition Composition

| A. Gels For the Topical Treatment of Acne | |
|---|---|
| 1. Hydroxypropyl cellulose | 1 g |
| Butylhydroxy toluene | 0.05 g |
| 3-O-etretinoyl (all trans) clindamycin | 0.5 g |
| Isopropanol, sufficient amount for | 100 g |
| 2. Hydroxypropyl cellulose | 1 g |
| Butylhydroxy toluene | 0.05 g |
| 2'-O-[7-(5,8-dimethyl-6-methoxy-2-naphthyl)-3-methyl-2E, 4E, 6E-octatrienoyl]-erythromycin A | 0.5 g |
| Isopropanol, sufficient amount for | 100 g |
| 3. Hydroxypropyl cellulose | 1.5 g |
| Butylhydroxy toluene | 0.05 g |
| 2'-O-[7-5,8,-dimethyl-6-methoxy-2-naphthyl)-3-methyl-2E, 4E, 6E-octatrienoyl]-roxithromycin | 0.3 g |
| Isopropanol, sufficient amount for | 100 g |
| B. Lotions For The Topical Treatment of Acne | |
| 1. Butylhydroxy toluene | 0.05 g |
| 2'-O-etretinoyl (all trans) erythromycin A | 1 g |
| Triglycerides of $C_8$–$C_{12}$ fatty acids, sufficient amount for | 100 g |
| 2. Butylhydroxy toluene | 0.05 g |
| 2'-O-[4-[4-(2,3,6-trimethyl-4- | 1 g |

-continued

| | |
|---|---|
| methoxy phenyl)-2-methyl-1E, 3E-butadiene]yl-benzoyl]-roxithromycin | |
| Isopropanol | 50 g |
| Triglycerides of $C_8$-$C_{12}$ fatty acids, sufficient amount for | 100 g |

In this Example, the active compound can be replaced by the same amount of 2'-O-[7-(5,8-dimethyl-6-methoxy-2-naphthyl)-3-methyl-2E, 4E, 6E-octatrienoyl]-erythromycin A.

| C. Sticks For The Topical Treatment of Acne | |
|---|---|
| 1. White petrolatum | 52 g |
| Petrolatum oil | 15 g |
| Refined paraffin | 32 g |
| 2'-O-etretinoyl (all trans) erythromycin A | 1 g |
| 2. White petrolatum | 52 g |
| Petrolatum oil | 15 g |
| Refined paraffin | 32 g |
| 2'-O-[7-(5,8-dimethyl-6-methoxy-2-naphthyl)-3-methyl-2E, 4E, 6E-octatrienoyl]-erythromycin A | 1 g |

What is claimed is:

1. An ester of the etretinic type or related to a macrolide or lincosamide having the formula

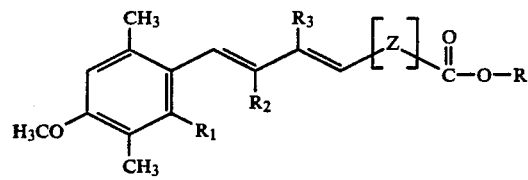

wherein
R represents a macrolide selected from the group consisting of:
erythromycin A substituted in the 2' position,
roxithromycin substituted in the 2'position,
oleandomycin substituted in the 2' position,
oleandomycin substituted in the 4" position,
oleandomycin substituted in the 2' and 4" positions,
josamycin substituted in the 9 position,
josamycin substituted in the 2' position,
josamycin substituted in the 9 and 2' positions,
spiramycin (I) substituted in the 2' position,
spiramycin (I) substituted in the 4" position,
spiramycin (I) substituted in the 2' and 4" positions,
spiramycin (II) substituted in the 2' position,
spiramycin (II) substituted in the 4" position,
spiramycin (II) substituted in the 2' and 4" positions,
spiramycin (III) substituted in the 2' position,
spiramycin (III) substituted in the 4" position,
spiramycin (III) substituted in the 2' and 4" positions,
or R represents a lincosamide selected from the group consisting of:
lincomycin substituted in the 3 position,
clindamycin substituted in the 3 position,
lincomycin substituted in the 2, 4 and 7 positions and
clindamycin substituted in the 2 and 4 positions,
$R_1$ represents methyl,
$R_2$ represents hydrogen, or $R_1$ and $R_2$ together form a vinylene (—CH=CH—) radical,
$R_3$ represents hydrogen or alkyl having 1–4 carbon atoms, and
Z represents a divalent radical (1) of the formula

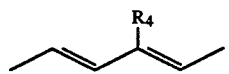

wherein $R_4$ represents hydrogen or alkyl having 1–4 carbon atoms or (2) of the formula the isomers, mixtures and salts of said ester.

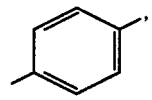

2. The ester of claim 1 selected from the group consisting of
2'-O-etretinoyl (all trans) roxithromycin,
2'-O-etretinoyl (all trans) erythromycin A,
3'-O-etretinoyl (all trans) lincomycin,
3'-O-etretinoyl (all trans) clindamycin,
2'-O-etretinoyl (all trans) oleandomycin,
2'and 9-O-etretinoyl (all trans) josamycin,
2'-O-etretinoyl (all trans) spiramycin (I), (II) and (III),
2'-O-[7-(5,8-dimethyl-6-methoxy-2-naphthyl)-3-methyl-2E, 4E, 6E-octatrienoyl]-erythromycin A,
2'-O-[7-(5,8-dimethyl-6-methoxy-2-naphthyl)-3-methyl-2E, 4E, 6E-octatrienoyl]-oleandomycin,
3'-O-[4-[4-(2,3,6-trimethyl-4-methoxy phenyl)-2-methyl-1E,3E-butadiene]yl benzoyl]-erythromycin A,
3'-O-[4[4-(2,3,6-trimethyl-4-methoxy phenyl)-2-methyl-1E, 3Ebutadiene]yl benzoyl]-clindamycin,
2'-O-[7-(5,8-dimethyl-6-methoxy,-2-naphthyl)-3-methyl-2E, 4E, 6E-octatrienoyl]-roxithromycin, and
2'-O-[4-[4-(2,3,6-trimethyl,-4-methoxy phenyl)-2-methyl-1E, 3E-butadiene]yl benzoyl]-roxithromycin.

3. A pharmaceutical or cosmetic composition for the treatment of dermatoses comprising in an anhydrous vehicle, as the active component, a pharmaceutically or cosmetically effective amount of at least one ester of claim 1.

4. The composition of claim 3 wherein said ester is present in an amount ranging from 0.001 to 10 weight percent based on the total weight of said composition.

5. The composition of claim 3 wherein said ester is present in an amount ranging from 0.01 to 1 weight percent based on the total weight of said composition.

6. The composition of claim 3 wherein said anhydrous vehicle is acetone, isopropyl alcohol, triglycerides of fatty acids, $C_1$–$C_4$ alkyl ester of a short chain acid, poly tetrahydrofuran ether, a silicone or a mixture thereof.

7. The composition of claim 3 which also contains a thickening agent in an amount ranging from 0.5 to 20 weight percent based on the total weight of said composition.

8. The composition of claim 7 wherein said thickening agent is a cellulose derivative.

9. The composition of claim 3 which also contains one or more of an antioxidant, a preservative, a perfume, a colorant or another anti-acne or anti-psoriasic agent.

* * * * *